(12) United States Patent
Edell et al.

(10) Patent No.: US 7,241,451 B1
(45) Date of Patent: Jul. 10, 2007

(54) COMPOSITION FOR REDUCING THE APPEARANCE OF SCARS

(75) Inventors: Drew Edell, Upper Montclair, NJ (US); Kenneth Klein, Fair Lawn, NJ (US)

(73) Assignee: CCA Industries, Inc., East Rutherford, NJ (US)

( * ) Notice: Subject to any disclaimer, the term of this patent is extended or adjusted under 35 U.S.C. 154(b) by 548 days.

(21) Appl. No.: 10/314,580

(22) Filed: Dec. 9, 2002

(51) Int. Cl.
 *A61K 6/00* (2006.01)
 *A61K 8/00* (2006.01)
(52) U.S. Cl. .......................................... 424/401; 424/59
(58) Field of Classification Search ................ 424/401, 424/59
See application file for complete search history.

(56) References Cited

U.S. PATENT DOCUMENTS

| | | | | |
|---|---|---|---|---|
| 5,837,270 | A | * | 11/1998 | Burgess ....................... 424/401 |
| 6,197,281 | B1 | * | 3/2001 | Stewart et al. ................. 424/59 |
| 6,322,776 | B1 | * | 11/2001 | Ortega et al. .................. 424/59 |
| H2013 | H | | 2/2002 | Boyd et al. |
| 2003/0072726 | A1 | * | 4/2003 | Banister et al. ............... 424/62 |

OTHER PUBLICATIONS

Quinn et al; Non-pressure treatment of hypertrophic scars, Apr. 10, 1985; Burns vol. 12, pp. 102-108.
Tac Ahm, MD et al;Topical silicone gel: A new treatment for hypertrophic scars; Mar. 8, 1989; Surgery Oct. 1989; pp. 781-787.
Saulis MD et al; Effect of Mederma on Hypertrophic Scarring in the Rabbit Ear Model; Jul. 2002, Plastic and Reconstructive Surgery; pp. 177-186.
Mustoe MD et al; International Clinical Recommendations on Scar Management; Aug. 2002; Plastic and Reconstructive Surgery; pp. 560-571.
Mercer; Silicone gel in the treatment of keloid scars; 1989; British Journal of Plastic Surgery; pp. 83-87.
Katz MD, Silicone Gel Sheeting in Scar Therapy; Jul. 1995; Cuts, vol. 56, pp. 65-67.

* cited by examiner

*Primary Examiner*—Lakshmi S. Channavajjala
(74) *Attorney, Agent, or Firm*—Fattibene & Fattibene; Paul A. Fattibene; Arthur T. Fattibene

(57) ABSTRACT

A cream or ointment for topical application to reduce the appearance of scars. A silicone compound is combined with a sunscreen or sun block for topical application that helps fade or diminish scar tissue making the scar less noticeable. The silicone compound acts as a protective barrier and prevents epidermal water loss that aids in the healing and reduction of scar tissue. The sunscreen or sun block prevents the new tissue from being damaged and protects the scar tissue from the effects of ultraviolet radiation, resulting in more uniform skin color reducing the appearance of the scar tissue. Vitamins E and K1, as well as onion extract, are also included for improving the appearance of scars. The cream or ointment of the present invention may be massaged into the area of the scar twice daily for two to three minutes at a time. The cream or ointment is easy to apply and is a cost effective method to reduce the appearance of scars.

2 Claims, 1 Drawing Sheet

COMPOSITION FOR REDUCING THE APPEARANCE OF SCARS

FIELD OF THE INVENTION

The present invention relates in general to the treatment of scars, and particularly to a silicone and sunscreen based topical cream for placement on scar tissue to improve the appearance of the scar.

BACKGROUND OF THE INVENTION

A scar is a mark left on damaged tissue after it has healed. The body repairs wounds by increasing production of the fibrous protein collagen at the site of the damage. The collagen helps form new connective tissue, which covers the area of the wound. Often, a hypertrophic scar may form that is large and unsightly. A keloid scar may also form into a large irregular shaped scar that may continue to grow in size. Often, the scars are of a different color than the surrounding skin. The scars may also be more susceptible to damage by ultraviolet rays of the sun.

There have been many studies on scar management for the treatment of scars in an effort to reduce their appearance. Elastic compression garments have been used in the prevention and treatment of scars. Other efforts to treat scars and improve their appearance have included steroid injections, surgical revision, radiation, laser, cryotherapy, compression, and a combination of these treatments. Even with these treatments, high rates of reoccurrence have occurred. Additionally, many of these treatments are painful and expensive.

Many studies have found silicone gel sheeting or pads to be successful in the management of hypertrophic and keloid scars. While the mechanism of action of silicone gel sheeting is unclear in the treatment of scar tissue, it has developed interest because of its simplicity and ease of use. However, the silicone gel pads or sheets are often difficult to hold in place. The silicone gel sheets or pads have often been held in place over scar tissue by crepe bandages, tape, or compression garments. However, placement and holding in place of silicone gel pads in the treatment of scar tissue is not convenient, and sometimes results in minor complications such as maceration, skin erosion, rash, or pruritus or itching. Therefore, there is a need for an easier to use treatment for scar tissue management and to reduce the appearance of scars that can be easily used and applied by a patient with little risk of any complications.

SUMMARY OF THE INVENTION

The present invention comprises a topical cream containing silicone and sunscreen that is easily applied. A silicone compound in an emulsion combined with sunscreen forms a topical cream that is massaged into a scar area. A combination of protective oil, silicone, wax, and sunscreen is combined to provide a compound that aids in scar tissue management. Three silicones, such as dimethicone, cetyl dimethicone, dimenthicone copolyol, are combined with a sun screen or blocker, such as octyl methoxycinnamate or zinc oxide. The combination of these two elements, silicone and a sun screen or sun blocker, improves the appearance of scar tissue by flattening and softening the scar tissue and preventing adverse affects from the sun on the scar tissue, providing more uniform coloration and reduced visibility of the scar tissue, and therefore its appearance.

Accordingly, it is an object of the present invention to reduce the appearance of scars.

It is a further object of the present invention to prevent scar tissue discoloration.

It is an advantage of the present invention that it helps raised and discolored scars to become softer, flatter and less visible.

It is a further advantage of the present invention that it is easy to apply.

It is a feature of the present invention that it contains silicone and sunscreen.

It is a further feature of the present invention that it is in the form of a topical cream that is rubbed onto the scar tissue area.

These and other objects, advantages, and features will become more readily apparent in the following detailed description.

DETAILED DESCRIPTION OF THE PREFERRED EMBODIMENTS

Figure 1:
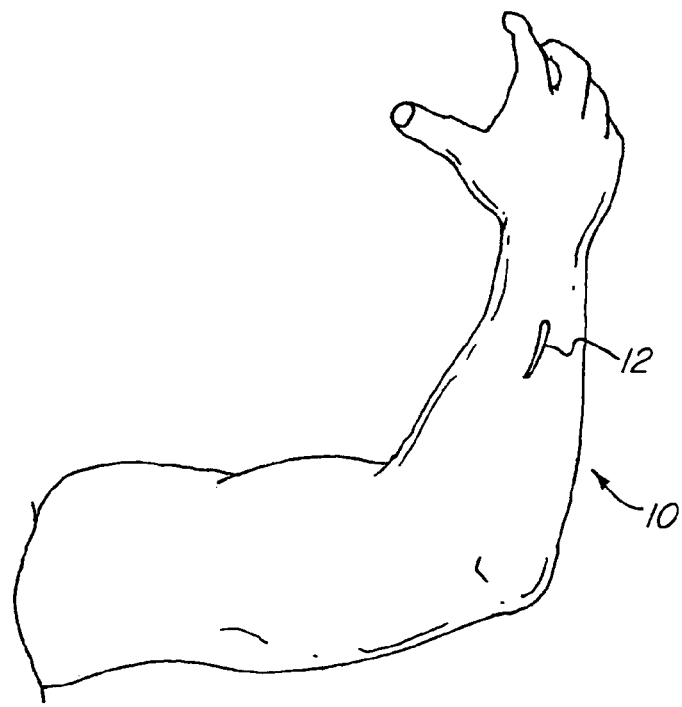
FIG. 1 schematically illustrates an individual's arm having a scar thereon.

FIG. 1 schematically illustrates a patient's or individual's arm 10 illustrating a scar 12 thereon.

Figure 2:
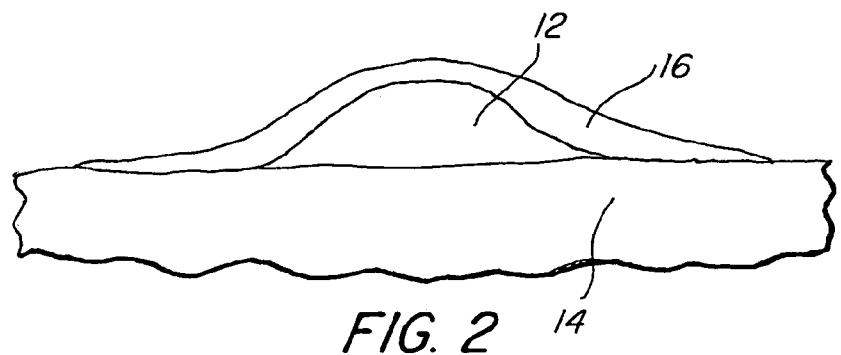
FIG. 2 schematically illustrates scar tissue and the application of the present invention.

FIG. 2 schematically illustrates hypertrophy or excessive scar tissue growth and the application of the topical cream or ointment of the present invention. Hypertrophic scar tissue 12 is illustrated on skin or dermal tissue 14. The cream 16 of the present invention is schematically illustrated as topically applied to the scar tissue 12 and surrounding skin or dermis 14.

Figure 3:
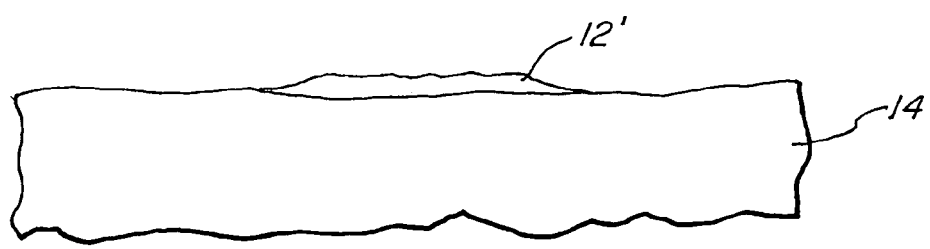
FIG. 3 schematically illustrates the improved appearance of scar tissue.

FIG. 3 schematically illustrates the improved appearance of the flattened and softened tissue 12' on the skin or dermis 14.

The cream or ointment of the present invention instantly begins reducing the appearance of scars by helping them to fade, diminish and become less noticeable. The topically applied cream or ointment of the present invention helps raised and discolored scars become flatter, softer, smoother and closer to the skin's natural tone. The present invention helps reduce the appearance of new wounds that have healed and older scars that are still visible. The cream or ointment of the present invention is massaged gently into a scarred area. The present invention may be applied twice a day and massaged for two to three minutes upon each application. The massaging of the ointment or cream of the present invention into the scar area aids in breaking up collagen or scar tissue, reducing the appearance of the scar tissue.

The cream or ointment of the present invention combines silicone compounds and a sun blocker. The silicone compounds may be for example dimethicone, cetyl dimethicone, dimethicone copolyol or other equivalent silicone compounds. The cream or ointment of the present invention may be an oil silicone and water emulsion containing a mixture of protective oils, silicones and waxes. A mixture of vitamins, such as Vitamin E and K1, as well as an onion extract, may be included in the cream or ointment of the present invention.

A sunscreen or sun blocker, such as octyl methoxycinnate or zinc oxide may be used in the cream or ointment of the present invention. Other known or equivalent sunscreens or sun blockers may also be used. For example other known sunscreens or sun blockers may include, aminobenzoic acid, cinoxate, octinoxate, titanium dioxide, zinc oxide, avobenzone, trolamine salicylate, octisalate, ensulizole, meradimate, octocrylene, oxybenzone, dioxybenzone, sulisobenzone, padimate O, homosalate, and others.

The silicone acts as a protective barrier to the skin that reduces trans-epidermal water loss that helps to increase collagenase activity. This results in the reduction of collagen formation and reduces the appearance of scars. The silicone also provides an environment facilitating the skin's natural healing and reparative properties that work to reduce the appearance of scars over time. The silicone also prevents viruses and bacteria from penetrating that may interfere with skin cells.

The sunscreen or sun block component of the present invention protects the scar tissue from ultraviolet radiation. Ultraviolet radiation may damage newly laid collagen as well as result in hardening of elastin. Additionally, hyperpigmentation is prevented so the scar tissue will not become discolored and blends in with the surrounding tissue. This makes the scar appear less noticeable.

The scar diminishing cream should contain a therapeutically effective amount of silicone compound and a therapeutically effective amount of sunscreen or sunblock. By therapeutically effective it is meant an amount sufficient to induce a positive benefit, and preferably to reduce the appearance of a scar.

The present invention may have a formulation in accordance with Table 1 below.

TABLE 1

| No. | Phase | Ingredient | INCI/Chemical Designation | Percent Range by Weight |
|---|---|---|---|---|
| 1 | A | GE SF 1528 | DIMETHICONE COPOLYOL | 1.0–7.0 |
| 2 | A | ESCALOL 557 | OCTINOXATE | 2.0–7.5 |
| 3 | A | ELFACOS ST-37 | PEG-22/DODECYL GLYCOL COPOLYMER | 0.5–3.0 |
| 4 | A | MYRITOL 318 | CAPRYLIC/CAPRIC TRIGLYCERIDE | 2.0–8.0 |
| 5 | A | PURESYN 2 | HYDROGENATED POLYDECECENE | 1.5–7.5 |
| 6 | A | DC 200-100 | DIMETHICONE | 0.5–3.0 |
| 7 | A | ABIL WAX 9801 | CETYL DIMETHICONE | 0.5–3.5 |
| 8 | A | CAB-O-SIL M5 | SILICA | 0.2–2.0 |
| 9 | A | Z-COTE HP1 | ZINC OXIDE (AND) DIMETHICONE | 0.5–7.5 |
| 10 | A | ARLACEL P135 | PEG-30 DIPOLYHYDROXYSTEARATE | 0.5–5.0 |
| 11 | A | CASTORWAX MP70 | HYDROGENATED CASTOR OIL | 0.5–5.0 |
| 12 | A | VITAMIN E ACETATE | TOCOPHERYL ACETATE | 0.05–1.0 |
| 13 | B | DEIONIZED WATER | WATER | 50.0–82.0 |
| 14 | B | CARBOWAX 400 | PEG-8 | 0.75–2.5 |
| 15 | B | PLANTAREN 1200N | LAURYL GLUCOSIDE | 0.05–2.0 |
| 16 | B | SODIUM CHLORIDE | SODIUM CHLORIDE | 0.1–1.5 |
| 17 | B | GLYDANT | DMDM HYDANTOIN | 0.1–0.5 |
| 18 | B | VITAMIN K1 | PHYTONADIONE | 0.1–0.75 |
| 19 | B | ONION EXTRACT | ALLIUM CEPA(ONION) BULB EXTRACT | 0.1–2.0 |

The Table 2 below identifies the general function of the chemical ingredient in the formulation.

TABLE 2

| No. | Phase | INCI/Chemical Designation | Ingredient Function |
|---|---|---|---|
| 1 | A | DIMETHICONE COPOLYOL | W/O EMULSIFIER |
| 2 | A | OCTINOXATE | UVB SUNSCREEN |
| 3 | A | PEG-22/DODECYL GLYCOL COPOLYMER | THICKENER/STABILIZER |
| 4 | A | CAPRYLIC/CAPRIC TRIGLYCERIDE | EMOLLIENT |
| 5 | A | HYDROGENATED POLYDECECENE | EMOLLIENT |
| 6 | A | DIMETHICONE | EMOLLIENT |
| 7 | A | CETYL DIMETHICONE | STABILIZER |
| 8 | A | SILICA | THICKENER/STABILIZER |
| 9 | A | ZINC OXIDE (AND) DIMETHICONE | UVB/UVA SUNSCREEN |
| 10 | A | PEG-30 DIPOLYHYDROXYSTEARATE | W/O EMULSIFIER |
| 11 | A | HYDROGENATED CASTOR OIL | THICKENER/STABILIZER |

TABLE 2-continued

| No. | Phase | INCI/Chemical Designation | Ingredient Function |
|---|---|---|---|
| 12 | A | TOCPHERYL ACETATE | ANTIOXIDANT |
| 13 | B | WATER | HUMECTANT |
| 14 | B | PEG-8 | EMULSIFIER/HUMECTANT |
| 15 | B | LAURYL GLUCOSIDE | EMULSIFIER/HUMECTANT |
| 16 | B | SODIUM CHLORIDE | STABILIZER |
| 17 | B | DMDM HYDANTOIN | PRESERVATIVE |
| 18 | B | PHYTONADIONE | SKIN ENHANCER |
| 19 | B | ALLIUM CEPA(ONION) BULB EXTRACT | SKIN ENHANCER |

A preferred formulation is indicated in Table 3 below.

TABLE 3

| No. | Phase | Ingredient | Percent by Weight | Batch Size for 1,000.00 |
|---|---|---|---|---|
| 1 | A | GE SF 1528 | 3.00 | 30.00 |
| 2 | A | ESCALOL 557 | 7.50 | 75.00 |
| 3 | A | ELFACOS ST-37 | 3.00 | 30.00 |
| 4 | A | MYRITOL 318 | 5.00 | 50.00 |
| 5 | A | PURESYN 2 | 3.00 | 30.00 |
| 6 | A | DC 200-100 | 2.00 | 20.00 |
| 7 | A | ABIL WAX 9801 | 2.00 | 20.00 |
| 8 | A | CAB-O-SIL M5 | 0.50 | 5.00 |
| 9 | A | Z-COTE HP1 | 3.00 | 30.00 |
| 10 | A | ARLACEL P135 | 3.25 | 32.50 |
| 11 | A | CASTORWAX MP70 | 2.50 | 25.00 |
| 12 | A | VITAMIN E ACETATE | 0.10 | 1.00 |
| 13 | B | DEIONIZED WATER | 59.80 | 598.00 |
| 14 | B | CARBOWAX 400 | 3.00 | 30.00 |
| 15 | B | PLANTAREN 1200N | 0.10 | 1.00 |
| 16 | B | SODIUM CHLORIDE | 1.00 | 10.00 |
| 17 | B | GLYDANT | 0.20 | 2.00 |
| 18 | B | VITAMIN K1 | 0.05 | 0.50 |
| 19 | B | ONION EXTRACT | 1.00 | 10.00 |
|   |   | TOTAL | 100.00 | 1,000.00 |

In manufacturing the cream or ointment of the invention, phase A ingredients are mixed or combined together and are heated to 90° C. Phase B ingredients are mixed or combined together and are heated to 50° C. Phase A ingredients and phase B ingredients are combined. The combined two phases are homogenized or mixed. The cream or ointment is then allowed to cool and then packaged.

The formulation may be referred to as a water-in-oil emulsion using silicon. The silicon compound is in the external or continuous phase. This assures quick and uniform contact with the scar tissue, thus promoting a reduction in the appearance of the scar.

The topical application of the present invention to scar tissue is easy and convenient, and greatly helps to fade, diminish, and make less visible the appearance of scars. The cream or ointment of the present invention is fast absorbing and will not stain clothing. Additionally, it can be worn under makeup. The scar appearance diminishing ointment or cream of the present invention may be used on all scar tissues, such as hypertrophic scars and keloid scars, to reduce their appearance. The cream or ointment is easily topically applied by an individual on the area of the scar tissue. The cream or ointment is safe and effective, with substantially no risk of adverse affects or skin irritation.

Although the preferred embodiment has been illustrated and described, it will be obvious to those skilled in the art that various modifications may be made without departing from the spirit and scope of this invention.

What is claimed is:

1. A scar appearance reducing topical cream comprising:
   dimethicone copolyol ranging between 1.0 to 7.0 percent by weight;
   octinoxate ranging between 2.0 to 7.5 percent by weight;
   zinc oxide ranging between 0.5 to 7.5 percent by weight;
   PEG-30 dipolyhydroxystearate between 0.5 to 5.0 percent by weight;
   vitamin K1 between 0.01 to 0.75 percent by weight; and
   onion extract between 0.1 and 2.0 percent by weight.

2. A scar appearance reducing topical cream comprising:
   about 3.00 percent by weight of dimethicone copolyol;
   about 7.50 percent by weight of octinoxate;
   about 3.00 percent by weight of PEG-22/dodecyl glycol copolymer;
   about 5.00 percent by weight of caprylic/capric triglyceride;
   about 3.00 percent by weight of hydrogenated polydecene;
   about 2.00 percent by weight of dimethicone;
   about 2.00 percent by weight of cetyl dimethicone;
   about 0.50 percent by weight of silica;
   about 3.00 percent by weight of zinc oxide;
   about 3.25 percent by weight of PEG-30 dipolyhydroxystearate;
   about 2.50 percent by weight of hydrogenated castor oil;
   about 0.10 percent by weight of tocopheryl acetate;
   about 59.80 percent by weight of deionized water;
   about 3.00 percent by weight of PEG-8;
   about 0.10 percent by weight of lauryl glucoside;
   about 1.00 percent by weight of sodium chloride;
   about 0.20 percent by weight of DMDM hydantoin;
   about 0.50 percent by weight of phytonadione; and
   about 1.00 percent by weight of an *allium cepa* bulb extract.

* * * * *